(12) United States Patent
Walter et al.

(10) Patent No.: US 8,198,215 B2
(45) Date of Patent: Jun. 12, 2012

(54) METHODS FOR PROTECTING SEEDS

(75) Inventors: Harald Walter, Rodersdorf (CH);
Ronald Zeun, Neuenburg (DE); Josef Ehrenfreund, Allschwil (CH); Hans Tobler, Basel (CH); Camilla Corsi, Basel (CH); Clemens Lamberth, Efringen-Kirchen (DE)

(73) Assignee: Sygenta Crop Protection LLC, Greensboro, NC (US)

( * ) Notice: Subject to any disclaimer, the term of this patent is extended or adjusted under 35 U.S.C. 154(b) by 946 days.

(21) Appl. No.: 11/573,411

(22) PCT Filed: Aug. 11, 2005

(86) PCT No.: PCT/EP2005/008752
§ 371 (c)(1),
(2), (4) Date: Feb. 8, 2007

(87) PCT Pub. No.: WO2006/015866
PCT Pub. Date: Feb. 16, 2006

(65) Prior Publication Data
US 2009/0054233 A1    Feb. 26, 2009

(51) Int. Cl.
*A01N 43/56*    (2006.01)
*A01P 3/00*    (2006.01)

(52) U.S. Cl. ........................ 504/100; 514/406

(58) Field of Classification Search .................. 514/406; 504/100
See application file for complete search history.

(56) References Cited

FOREIGN PATENT DOCUMENTS
WO    03074491 A    9/2003

*Primary Examiner* — John Pak
(74) *Attorney, Agent, or Firm* — Kody Jones

(57) ABSTRACT

A method of controlling phytopathogenic diseases on useful plants or plant propagation material thereof, which comprises applying to said plant propagation material a fungicidally effective amount of a compound of formula (I) wherein $R_1$ is trifluoromethyl or difluoromethyl and $R_2$ is hydrogen or methyl, or a tautomer of such a compound, is particularly effective in controlling or preventing fungal diseases of crop plants.

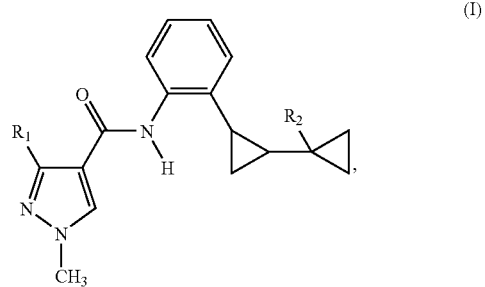

7 Claims, No Drawings

METHODS FOR PROTECTING SEEDS

This application is a 371 of International Application No. PCT/EP2005/008752 filed Aug. 11, 2005, which claims priority to GB 0418048.5 filed Aug. 12, 2004, the contents of which are incorporated herein by reference.

The present invention relates to a method for protecting useful plants or plant propagation material, such as seed, with a fungicide against phytopathogenic diseases, to plant propagation material protecting compositions comprising said fungicide and to plant propagation material treated by said compositions.

The protection of useful plants or plant propagation material thereof by applying pesticides to the plant propagation material is a targeted pesticide application which addresses the need for a reduction of environmental and worker exposure compared to foliar or soil pesticide applications.

From WO 03/074491 it is known that certain ortho-cyclopropyl-carboxanilide derivatives have biological activity against phytopathogenic fungi. WO 03/074491 also describes methods of controlling infestation of cultivated plants by phytopathogenic microorganisms by application of said ortho-cyclopropyl-carboxanilide derivatives to plants, to parts thereof or to the locus thereof. Said described methods are for example foliar application, application by drenching the locus of the plant with a liquid formulation, application of granulates to the soil, application of granulates to flooded crop cultivation fields, such as flooded rice fields, and seed treatment. WO 03/074491 specifically teaches on page 26 of the specification that under said methods foliar application is the preferred method of application.

Surprisingly it was found that a specific subgroup of said ortho-cyclopropyl-carboxanilide derivatives is especially suitable for seed treatment application.

It is therefore proposed in accordance with the present invention a method of controlling phytopathogenic diseases on useful plants or plant propagation material thereof, which comprises applying to said plant propagation material a fungicidally effective amount of a compound of formula I

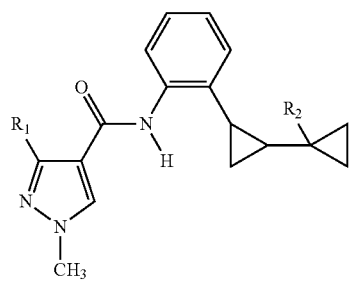

(I)

wherein
$R_1$ is trifluoromethyl or difluoromethyl and
$R_2$ is hydrogen or methyl; or a tautomer of such a compound.

The method according to the invention is especially suitable to increase the yield and/or quality of useful plants, such as crop yield of crop plants.

Accordingly the present invention also relates to a method of protecting plant propagation material and organs that grow at a later point in time against damage phytopathogenic diseases, which method comprises applying to said propagation material a fungicidally effective amount of a compound of formula I.

Accordingly the present invention further relates to a method of improving the growing characteristics of a plant, which method comprises applying to said propagation material a fungicidally effective amount of a compound of formula I.

The compounds of formula I occur in different stereoisomeric forms, which are described in formulae $I_I$, $I_{II}$, $I_{III}$ and $I_{IV}$:

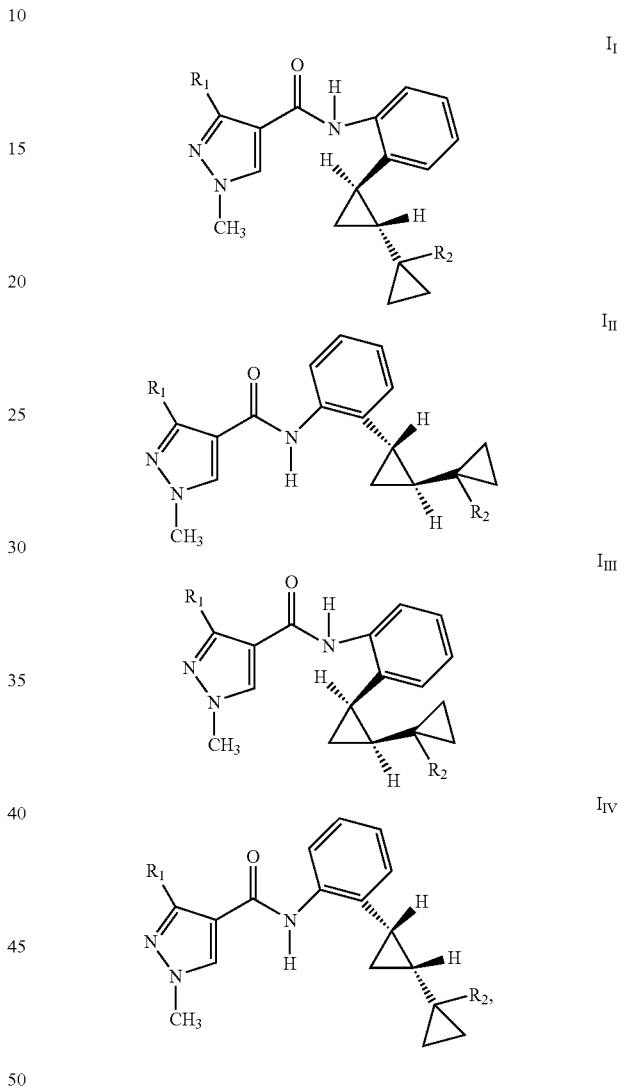

wherein $R_1$ and $R_2$ are as defined under formula I. The methods according to the invention cover the application of all such stereoisomers and mixtures thereof to plant propagation material in any ratio.

In a preferred embodiment of the present invention a compound of formula I, wherein $R_1$ is difluoromethyl and $R_2$ is hydrogen is applied to plant propagation material.

In a preferred embodiment of the present invention a compound of formula I, wherein $R_1$ is difluoromethyl and $R_2$ is methyl is applied to plant propagation material.

In a preferred embodiment of the present invention a compound of formula I, wherein $R_1$ is trifluoromethyl and $R_2$ is hydrogen is applied to plant propagation material.

In a preferred embodiment of the present invention a compound of formula I, wherein $R_1$ is trifluoromethyl and $R_2$ is methyl is applied to plant propagation material.

In a further preferred embodiment of the present invention a compound of formula Ia (trans)

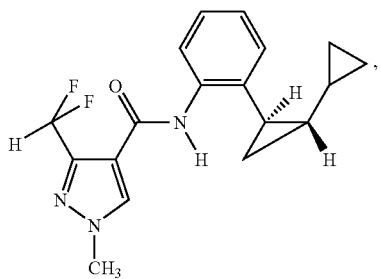
(Ia)

which represents a compound of formula $I_I$, wherein $R_1$ is difluoromethyl and $R_2$ is hydrogen; a compound of formula $I_{II}$, wherein $R_1$ is difluoromethyl and $R_2$ is hydrogen or a mixture in any ratio of a compound of formula $I_I$, wherein $R_1$ is difluoromethyl and $R_2$ is hydrogen, and a compound of formula $I_{II}$, wherein $R_1$ is difluoromethyl and $R_2$ is hydrogen, is applied to plant propagation material.

Among this embodiment of the invention preference is given to an embodiment, wherein a racemic compound of the formula Ia, which represent a racemic mixture of a compound of formula $I_I$, wherein $R_1$ is difluoromethyl and $R_2$ is hydrogen, and a compound of formula $I_{II}$, wherein $R_1$ is difluoromethyl and $R_2$ is hydrogen, is applied to plant propagation material.

In a further preferred embodiment of the present invention a compound of formula Ib (cis)

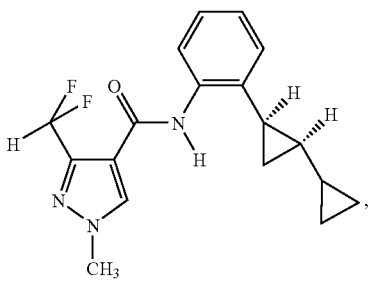
(Ib)

which represents a compound of formula $I_{III}$, wherein $R_1$ is difluoromethyl and $R_2$ is hydrogen; a compound of formula $I_{IV}$, wherein $R_1$ is difluoromethyl and $R_2$ is hydrogen or a mixture in any ratio of a compound of formula $I_{III}$, wherein $R_1$ is difluoromethyl and $R_2$ is hydrogen, and a compound of formula $I_{IV}$, wherein $R_1$ is difluoromethyl and $R_2$ is hydrogen, is applied to plant propagation material.

Among this embodiment of the invention preference is given to an embodiment, wherein a racemic compound of the formula Ib, which represents a racemic mixture of a compound of formula $I_{III}$, wherein $R_1$ is difluoromethyl and $R_2$ is hydrogen, and a compound of formula $I_{IV}$, wherein $R_1$ is difluoromethyl and $R_2$ is hydrogen, is applied to plant propagation material.

In a further preferred embodiment of the present invention a compound of formula Ic

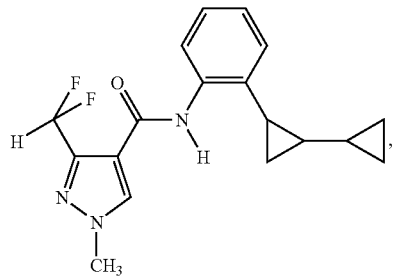
(Ic)

wherein the ratio of racemic compounds of formula Ia, which represent a racemic mixture of compounds of formula $I_I$, wherein $R_1$ is difluoromethyl and $R_2$ is hydrogen, and compounds of formula $I_{II}$, wherein $R_1$ is difluoromethyl and $R_2$ is hydrogen, to racemic compounds of formula Ib, which represent a racemic mixture of compounds of formula $I_{III}$, wherein $R_1$ is difluoromethyl and $R_2$ is hydrogen, and compounds of formula $I_{IV}$, wherein $R_1$ is difluoromethyl and $R_2$ is hydrogen, is from 1:1 to 100:1, is applied to plant propagation material.

Within said embodiment suitable ratios of racemic compounds of formula Ia, which represent a racemic mixture of compounds of formula $I_I$, wherein $R_1$ is difluoromethyl and $R_2$ is hydrogen, and compounds of formula $I_{II}$, wherein $R_1$ is difluoromethyl and $R_2$ is hydrogen, to racemic compounds of formula Ib, which represent a racemic mixture of compounds of formula $I_{III}$, wherein $R_1$ is difluoromethyl and $R_2$ is hydrogen, and compounds of formula $I_{IV}$, wherein $R_1$ is difluoromethyl and $R_2$ is hydrogen, are ratios such as 1:1, 2:1, 3:1, 4:1, 5:1, 6:1, 7:1, 8:1, 9:1, 10:1, 20:1, 50:1 or 100:1. Preference is given to ratios from 2:1 to 100:1, more preferably 4:1 to 10:1.

In a further preferred embodiment of the present invention a compound of formula Ic, wherein the content of racemic compounds of formula Ia, which represent a racemic mixture of compounds of formula $I_I$, wherein $R_1$ is difluoromethyl and $R_2$ is hydrogen, and compounds of formula $I_{II}$, wherein $R_1$ is difluoromethyl and $R_2$ is hydrogen, is from 65 to 99% by weight, is applied to plant propagation material.

In a further preferred embodiment of the present invention, a method of controlling phytopathogenic diseases on seeds of useful plants is disclosed, which comprises applying to the seeds a fungicidally effective amount of a mixture of compounds of the formula Ic

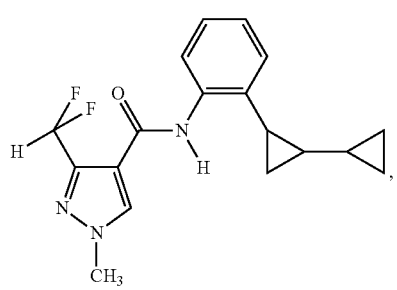
(Ic)

wherein the content of racemic compound of formula Ia (trans)

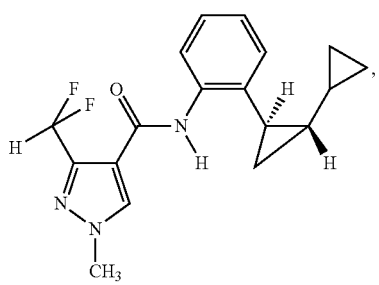

(Ia)

is from 65 to 99% by weight of the mixture, is applied to the seeds.

According to the instant invention, a "racemic mixture" of two enantiomers or a "racemic compound" means a mixture of two enantiomers in a ratio of substantially 50:50 of the two enantiomers.

An improvement in the growing (or growth) characteristics of a plant can manifest in a number of different ways, but ultimately it results in a better product of the plant. It can, for example, manifest in improving the yield and/or vigour of the plant or quality of the harvested product from the plant.

As used herein the phrase "improving the yield" of a plant relates to an increase in the yield of a product of the plant by a measurable amount over the yield of the same product of the plant produced under the same conditions, but without the application of the subject method. It is preferred that the yield be increased by at least about 0.5%, more preferred that the increase be at least about 1%, even more preferred is about 2%, and yet more preferred is about 4%, or more. Yield can be expressed in terms of an amount by weight or volume of a product of the plant on a specific basis. Said basis can be expressed in terms of time, growing area, weight of plants produced, amount of a raw material used, or the like.

As used herein the phrase "improving the vigour" of a plant relates to an increase or improvement of the vigour rating, or the stand (the number of plants per unit of area), or the plant height, or the plant canopy, or the visual appearance (such as greener leaf colour), or the root rating, or emergence, or protein content, or increased tillering, or bigger leaf blade, or less dead basal leaves, or stronger tillers, or less fertilizer needed, or less seeds needed, or more productive tillers, or earlier flowering, or early grain maturity, or less plant verse (lodging), or increased shoot growth, or earlier germination, or any combination of these factors, or any other advantages familiar to a person skilled in the art, by a measurable or noticeable amount over the same factor of the plant produced under the same conditions, but without the application of the subject method.

When it is said that a method is capable of "improving the yield and/or vigour" of a plant, the present method results in an increase in either the yield, as described above, or the vigor of the plant, as described above, or both the yield and the vigor of the plant.

A compound of formula I can also be used to treat stored products, such as grain, for protection against phytopathogenic diseases.

The methods according to the instant invention are particularly effective to protect useful plants or plant propagation material thereof against phytopathogenic fungi belonging to the following classes: Ascomycetes (e.g. the genus *Cochliobolus, Colletotrichum, Fusarium, Gaeumannomyces, Giberella, Monographella, Microdochium, Penicillium, Phoma, Pyricularia, Magnaporthe, Septoria, Pseudocercosporella, Tapesia* and *Thielaviopsis*); Basidiomycetes (e.g. the genus *Phakopsora, Puccinia, Rhizoctonia, Thanatephorus, Sphacelotheca, Tilletia, Typhula* and *Ustilago*); Fungi imperfecti (also known as Deuteromycetes; e.g. the genus *Ascochyta, Diplodia, Erysiphe, Fusarium, Helminthosporium, Phomopsis, Pyrenophora* and *Verticillium*); and Zygomycets (e.g. the genus *Rhizopus*).

According to the instant invention "useful plants" typically comprise the following species of plants: cereals, such as wheat, barley, rye or oats; beet, such as sugar beet or fodder beet; leguminous plants, such as beans, lentils, peas or soybeans; oil plants, such as rape, mustard, poppy, sunflowers, castor oil plants or groundnuts; cucumber plants, such as marrows, cucumbers or melons; fibre plants, such as cotton, flax, hemp or jute; vegetables, such as spinach, lettuce, asparagus, cabbages, carrots, onions, tomatoes, potatoes, cucurbits or paprika; lauraceae, such as avocados or camphor; maize; tobacco; rice; turf or ornamentals, such as flowers, shrubs, broad-leaved trees or evergreens, for example conifers. This list does not represent any limitation.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA(c), CryIF, CryIF(a2), CryIIA(b), CryIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). An example for a truncated toxin is a truncated CryIA(b), which is expressed in the Bt11 maize from Syngenta Seed SAS, as described below. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (*Coleoptera*), two-winged insects (*Diptera*) and butterflies (*Lepidoptera*).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin) YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); Nature-Gard® and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a CryIIIB (b1) toxin and has resistance to certain *Coleoptera* insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1 F for achieving resistance to certain *Lepidoptera* insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain *Lepidoptera*, include the European corn borer.

Transgenic crops of insect-resistant plants are also described in BATS (Zentrum für Biosicherheit und Nachhaltigkeit, Zentrum BATS, Clarastrasse 13, 405B Basel, Switzerland) Report 2003, (http://bats.ch).

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Useful plants of elevated interest in connection with present invention are cereals, such as wheat, rye, barley or oats; maize; turf; vegetables, such as tomatoes, cucurbits, beans and lettuce; potatoes; tobacco; sugarbeets; rice; lawns; cotton; soybeans; oil seed rape; pulse crops; sunflower; and ornamentals in horticulture. Under these useful plants of elevated interest, cereals may be particularly mentioned.

The term "plant propagation material" is understood to denote generative parts of a plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion.

Preferably "plant propagation material" is understood to denote seeds.

The method according to the present invention is particularly effective to protect useful plants or plant propagation material thereof against seedborne and soilborne diseases, such as *Alternaria* spp., *Ascochyta* spp., *Botrytis cinerea*, *Cercospora* spp., *Claviceps purpurea*, *Cochliobolus sativus*, *Colletotrichum* spp., *Epicoccum* spp., *Fusarium graminearum*, *Fusarium moniliforme*, *Fusarium oxysporum*, *Fusarium proliferatum*, *Fusarium solani*, *Fusarium subglutinans*, *Gäumannomyces graminis*, *Helminthosporium* spp., *Microdochium nivale*, *Penicillium* spp., *Phoma* spp., *Pyrenophora graminea*, *Pyricularia oryzae*, *Rhizoctonia solani*, *Rhizoctonia cerealis*, *Sclerotinia* spp., *Septoria* spp., *Sphacelotheca reilliana*, *Tilletia* spp., *Typhula incarnata*, *Urocystis occulta*, *Ustilago* spp. or *Verticillium* spp.; in particular against pathogens of cereals, such as wheat, barley, rye or oats; maize; rice; cotton; soybean; turf; sugarbeet; oil seed rape; potatoes; pulse crops, such as peas, lentils or chickpea; and sunflower.

The compounds of formula I or compositions comprising compounds of formula I according to the invention are particularly useful for controlling the following plant diseases:
*Ascochyta* species in pulse crops,
*Botrytis cinerea* (gray mold) in sunflower,
*Cochliobolus sativus* in cereals,
*Colletotrichum* species in pulse crops,
*Fusarium graminearum* in cereals and maize,
*Gäumannomyces graminis* in cereals and lawns,
*Helminthosporium maydis* in maize,
*Helminthosporium oryzae* in rice,
*Helminthosporium solani* on potatoes,
*Microdochium nivale* in wheat and rye,
*Pyrenophora graminea* in barley,
*Pyricularia oryzae* in rice,
*Rhizoctonia* species in cotton, soybean, cereals, maize, potatoes, rice and lawns,
*Sclerotinia homeocarpa* in lawns,
*Sphacelotheca reilliana* in maize,
*Tilletia* species in cereals,
*Typhula incarnata* in barley,
*Urocystis occulta* in rye,
*Ustilago* species in cereals and maize.

The compounds of formula I are applied by treating plant propagation material with a fungicidally effective amount of a compound of formula I. Preferably, compounds of formula I are applied by adhering compounds of formula I to plant propagation material in a fungicidally effective amount.

A preferred application method is seed treatment.

Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. It is believed that the treatment can be applied to the seed at any time between harvest of the seed and sowing of the seed or during the sowing process (seed directed applications).

The seed treatment occurs to an unsown seed, and the term "unsown seed" is meant to include seed at any period between the harvest of the seed and the sowing of the seed in the ground for the purpose of germination and growth of the plant.

Treatment to an unsown seed is not meant to include those practices in which the pesticide is applied to the soil but would include any application practice that would target the seed during the planting process.

Preferably, the treatment occurs before sowing of the seed so that the sown seed has been pre-treated.

The compounds of formula I may be applied before or after infection of the plant propagation material by the fungi.

The compounds of formula I are usually applied to the plant propagation material together with adjuvants customary in formulation technology. The compounds of formula I are preferably applied to plant propagation material in the form of compositions, but also can be applied to the plant propagation material simultaneously or in succession, with further compounds. These "further compounds" can be for example fertilizers, micronutrient donors, other preparations that influence plant growth, plant growth regulators, herbicides, insecticides, fungicides, bactericides, insect growth regulators, nematicides or molluscicides or mixtures of several of these preparations, such as two fungicides or a fungicide and an insecticide, if desired together with adjuvants, such as carriers, surfactants or other application-promoting adjuvants customarily employed in the art of formulation.

In a preferred embodiment the invention provides a method of controlling phytopathogenic diseases on useful plants or plant propagation material thereof, which comprises applying to said plant propagation material a fungicidally effective amount of a plant propagation material protecting composition comprising a compound of formula I together with a suitable carrier therefor.

A preferred application method is seed treatment.

The techniques of seed treatment application are well known to those skilled in the art, and they may be used readily in the context of the present invention. The compounds of formula I or plant propagation material protecting compositions comprising compounds of formula I together with a suitable carrier therefor can be formulated and applied as a slurry, a solid seed coating, a soak, or as a dust on the surface of the seed. There also may be mentioned, e.g., film-coating or encapsulation. The coating processes are well known in the art, and employ, for seeds, the techniques of film-coating or encapsulation, or for the other multiplication products, the techniques of immersion. Needless to say, the method of application of the compounds of formula I or of compositions comprising compounds of formula I together with a suitable carrier therefor to the seed may be varied and the invention is intended to include any technique which is to be used.

A preferred method of applying compounds of formula I or plant propagation material protecting compositions comprising compounds of formula I together with a suitable carrier therefor consists in spraying or wetting the plant propagation material with a liquid preparation, or mixing the plant material with a solid preparation of the compounds of formula I or plant propagation material protecting compositions comprising compounds of formula I together with a suitable carrier therefor.

The compounds of formula I or plant propagation material protecting compositions comprising compounds of formula I together with a suitable carrier therefor may be formulated or mixed in the seed treater tank or combined on the seed by overcoating with other seed treating agents. The agents to be mixed with the compounds of formula I or plant propagation material protecting compositions comprising compounds of formula I together with a suitable carrier therefor may be for the control of pests, modification of growth, nutrition, or for the control of plant diseases.

The plant propagation material protecting compositions applied to plant propagation material according to the instant invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such plant propagation material protecting compositions may be produced in conventional manner, e.g. by mixing the active ingredients with appropriate formulation inerts (solid or liquid carriers and optionally other formulating ingredients such as surface-active compounds (surfactants), biocides, anti-freezers, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

Such plant propagation material protecting compositions may comprise one or more further pesticides, for example a fungicide, acaricide, bactericide, insecticide, molluscicide, nematicide, rodenticide, two fungicides or a fungicide and an insecticide.

The term "carrier" according to the invention denotes a natural or synthetic, organic or inorganic material with which the compound of formula I is combined in order to facilitate its application to the plant, to the seeds or to the soil. This carrier is hence generally inert, and it must be agriculturally acceptable, in particular to the plant being treated. The carrier may be solid (clays, natural or synthetic silicates, silica, resins, waxes, solid fertilizers, and the like) or liquid (water, alcohols, ketones, petroleum fractions, aromatic or paraffinic hydrocarbons, chlorinated hydrocarbons, liquefied gases, and the like).

Solid carriers which may be used, for example for dusts and dispersible powders, are calcite, talc, kaolin, montmorilonite or attapulgite, highly-disperse silica or absorptive polymers. Possible particulate, adsorptive carriers for granules are pumice, crushed brick, sepiolite or bentonite, montmorillonite-type clay, and possible nonabsorbent carrier materials are calcite or dolomite.

Suitable liquid carriers are: aromatic hydrocarbons, in particular the fractions $C_8$ to $C_{12}$, such as xylene mixtures or substituted naphthalenes, phthalic esters such as dibutyl or dioctyl phthalate, aliphatic hydrocarbons such as cyclohexane or paraffins, alcohols and glycols as well as their ethers and esters, such as ethylene glycol monomethyl ether, ketones such as cyclohexanone, strongly polar solvents such as N-methyl-2-pyrrolidone, dimethyl sulfoxide or dimethylformamide, and, if appropriate, epoxidized vegetable oils or soybean oil; or water.

Suitable surface-active compounds are non-ionic, cationic and/or anionic surfactants having good emulsifying, dispersing and wetting properties, depending on the nature of the active ingredients to be formulated (whether only compounds of formula I or compounds of formula I in combination with other active ingredients). Surfactants will also be understood as meaning mixtures of surface-active compounds.

The surfactants customarily employed in formulation technology are described, inter alia, in the following publications:
"McCutcheon's Detergents and Emulsifiers Annual", MC Publishing Corp., Glen Rock, N.J., 1988.
M. and J. Ash, "Encyclopedia of Surfactants", Vol. I-III, Chemical Publishing Co., New York, 1980-1981.

Among the suitable surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols. The presence of at least one surfactant is often required because the active ingredients and/or the inert vehicles are not soluble in water and the carrier for the application is water.

Furthermore, particularly useful adjuvants which enhance application are natural or synthetic phospholipids from the series of the cephalins and lecithins, for example phosphatidylethanolamine, phosphatidylserine, phosphatidylglycerine or lysolecithin.

The plant propagation material protecting composition may also comprise at least one polymer from water-soluble and water-dispersible film-forming polymers that improve the adherence of at least the compounds of formula I to the treated plant propagation material, which polymer generally has an average molecular weight of at least 10,000 to about 100,000.

Typically a colouring agent, such as a dye or pigment, is included in the plant propagation material protecting composition, so that an observer can immediately determine that the plant propagation material is treated. Plant propagation material protecting compositions comprising a colouring agent are preferred embodiments of the plant propagation material protecting compositions according to the invention, as they improve user and consumer safety. The colouring agent is also useful to indicate to the user the degree of uniformity of the applied plant propagation material protecting composition.

Generally, the colouring agent tends to have a melting point above 30° C., and therefore, is suspended in the plant propagation material protecting composition of the present invention. The colouring agent can also be a soluble compound.

As examples of colouring agents may be mentioned pigment red 48-2 (CAS-7023-61-2), pigment blue 15 (CAS-147-14-8), pigment green 7 (CAS-1328-53-6), pigment violet 23 (CAS-6358-30-1), pigment red 53-1 (CAS-5160-02-1), pigment red 57-1 (CAS 5281-04-9), pigment red 112 (CAS 6535-46-2) or similar colouring agents.

The plant propagation material protecting compositions tend to comprise between 0.1 to 10% by mass of a colouring agent.

Whereas commercial products will preferably be formulated as concentrates (known as a pre-mix composition (or concentrate, formulated compound (or product)), the end user will normally employ diluted formulations, optionally also containing one or more other pesticide pre-mixes (known as a tank mix composition (or ready-to-apply, spray broth, or slurry)) for treatment of the propagation material, but can also be use appropriately formulated pre-mix compositions.

The tank-mix compositions are generally prepared by diluting with a solvent (for example, water) the one or more pre-mix compositions containing different pesticides, and optionally further auxiliaries. Generally, an aqueous tank-mix is preferred.

Accordingly, examples of plant propagation material compositions of inventions include tank-mix or slurry pesticidal compositions and pre-mix or pesticidal formulations.

In general, the formulations include from 0.01 to 90% by weight of active agent, from 0 to 20% agriculturally acceptable surfactant and 10 to 99.99% solid or liquid carries and adjuvant(s), the active agent consisting of at least the compound of formula I and optionally other active agents, particularly microbiocides or conservatives or the like.

Concentrated forms of compositions (such as pre-mix or pesticidal formulations) generally contain in between about 2 and 80%, preferably between about 5 and 70% by weight of active agent.

Tank-mix or slurry forms of concentrated forms of compositions (diluted formulations) may for example contain from 0.01 to 20% by weight, preferably from 0.01 to 5% by weight of active agent.

The amount of a compound of formula I used on the propagation material varies according type of propagation material (e.g., seed or tuber) and plant (for example, wheat seeds generally have less active ingredients adhered thereto than oil seed rape seeds based on equivalent weight of seeds), and is such that the effective fungicidal amount can be determined by biology trials.

When the compounds of formula I or plant propagation material protecting compositions comprising compounds of formula I together with a suitable carrier therefor are used for treating seed, rates of 0.1 to 5000 g of a compound of formula I per 100 kg of seed, preferably from 1 to 1000 g per 100 kg of seed, most preferably from 1 to 100 g per 100 kg of seed are generally sufficient.

In a further aspect of the invention, the invention provides a plant propagation material protecting composition comprising a compound of formula I, together with a suitable carrier therefor.

A preferred embodiment of this aspect of the invention is a plant propagation material protecting composition comprising a compound of formula I, together with a suitable carrier therefor, wherein said plant propagation material protecting composition comprises additionally a colouring agent.

In yet a further aspect of the invention, the invention provides plant propagation material treated with a plant propagation material protecting composition comprising a compound of formula I, together with a suitable carrier therefor.

A preferred embodiment of this aspect of the invention is plant propagation material treated with a plant propagation material protecting composition comprising a compound of formula I, together with a suitable carrier therefor, wherein said plant propagation material protecting composition comprises additionally a colouring agent.

The Examples which follow serve to illustrate the invention, "active ingredient" denoting a compound of formula I.

FORMULATION EXAMPLES

| Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Emulsifiable concentrate | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient | 5% | 6% | 4% |
| Talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient | 8% |
| polyethylene glycol (mol. wt. 200) | 3% |
| Kaolin | 89% |

The finely ground active ingridient is uniformly applied, in a mixer, to the kaolin moistened with polyethylene glycol. Non-dusty coated granules are obtained in this manner.

| Suspension concentrate | |
|---|---|
| active ingredient | 40% |
| propylene glycol | 10% |
| nonylphenol polyethylene glycol ether (15 mol of ethylene oxide) | 6% |
| Sodium lignosulfonate | 10% |
| Carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Flowable concentrate for seed treatment | |
|---|---|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples

Example B-1

Activity Against *Gäumannomyces Graminis* on Wheat

After application of the active ingredient formulated as a flowable concentrate for seed treatment onto seeds of winterwheat the seeds are sown in trays filled with field soil. The field soil has been inoculated artificially before sowing with *Gäumannomyces graminis* by thoroughly mixing mycelium and soil. The trial is kept in a growth room for 5 weeks at 17° C. and a 14 hr light period. The following assessments are made: % root browning. Each number is determined for 30 seeds per treatment (3 replicates a 10 seeds).

| Rate g Racemic Compound of formula Ia/100 kg seed | % root browning | Control |
|---|---|---|
| — | 50 | 0 |
| 33 | 20 | 60 |
| 10 | 28 | 44 |

Example B-2

Activity Against *Microdochium Nivale* on Wheat

After application of the active ingredient formulated as a flowable concentrate for seed treatment onto *M. nivale*-infected seeds of winterwheat the seeds are sown in trays filled with planting soil. The trial is kept for 4 weeks in a growth room at 4° C. and darkness. Then the temperature is increased to 15° C. and a 12 hr light period is provided. After development of the primary leaf plants are kept at 10° C. and high humidity until the trial is finished. The following assessments are made: number of infected plants. Each number is determined for 100 seeds per treatment (2 replicates a 50 seeds).

| Rate g Racemic Compound of formula Ia/100 kg seed | % infected plants | Control |
|---|---|---|
| — | 38 | 0 |
| 10 | 5 | 86.8 |

Example B-3

Activity Against *Pyrenophora Graminea* on Barley

After application of the active ingredient formulated as a flowable concentrate for seed treatment onto *P. graminea*-infected seeds of winterbarley the seeds are sown in trays filled with field soil. The trays are kept in a growth room for 3 weeks at 4° C. After this period the trial is transferred to a greenhouse where a temperature of 12° C. and a 14 hr light period is provided. The following assessments are made: number of infected plants. Each number is determined for 200 seeds per treatment (2 replicates a 100 seeds).

| Rate g Racemic Compound of formula Ia/100 kg seed | % infected plants | Control |
|---|---|---|
| — | 54 | 0 |
| 10 | 1 | 98.1 |

Example B-4

Activity Against *Ustilago Nuda* on Barley

After application of the active ingredient formulated as a flowable concentrate for seed treatment onto *U. nuda*-infected seeds of winterbarley the seeds are sown in trays filled with field soil. The trays are transferred to a growth room and kept there for 2 days at 20° C. and then for 2 weeks at 2° C. After this period the trial is transferred to a greenhouse where a temperature of 15° C. and a 14 hr light period is provided until flowering. The following assessments are made: number of infected heads. Each number is determined for 200 seeds per treatment (2 replicates a 100 seeds).

| Rate g Racemic Compound of formula Ia/100 kg seed | % infected heads | % Control |
|---|---|---|
| — | 23.1 | 0 |
| 5 | 0 | 100 |
| 2.5 | 0 | 100 |

Example B-5

Comparison Test with a Compound from the Prior Art: Activity Against *Ustilago Nuda* on Barley The activity against *Ustilago nuda* on barley of the racemic compound of formula Ia according to the invention was compared with racemic compound B, which is described as compound no. 2.69 on pages 7, table 2, and page 16, table 7, of WO 03/074491. The method used to compare the activity is described under example B-4 above.

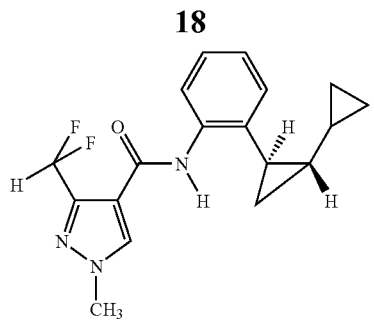

(compound of formula Ia according to the present invention)

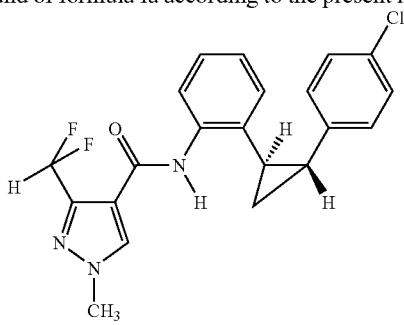

(compound B from the prior art)

| | Rate g active ingredient per 100 kg seed | % infected heads | % Control |
|---|---|---|---|
| — | — | 13 | 0 |
| Racemic compound of formula Ia | 10 | 0 | 100 |
| Racemic compound B | 10 | 11.9 | 9 |

The results show that, at an application rate of 10 g active ingredient per 100 kg seed, the racemic compound of formula Ia according to the present invention exerts a substantially better fungicidal action against *Ustilago nuda* on barley than racemic compound B from the prior art. In view of the structural similarity between the compounds, the enhanced action of the compounds according to the present invention were not to be expected.

Example B-6

Comparison Test with a Compound from the Prior Art: Activity Against *Ustilago Nuda* on Barley The activity against *Ustilago nuda* on barley of the racemic compound of formula Ia according to the invention was compared with racemic compound C (trans/cis-ratio: 10:1), which is described as compound no. 2.40 on pages 6 and 7, table 2, of WO 03/074491. The method used to compare the activity is described under example B-4 above.

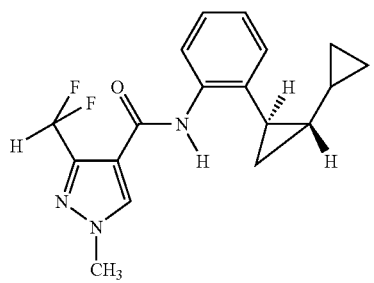

(compound of formula Ia according to the present invention)

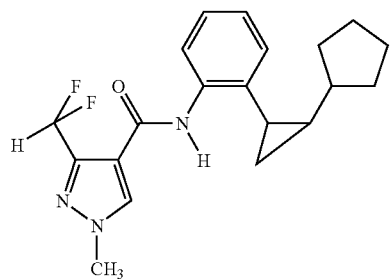

(compound C from the prior art)

|  | Rate g active ingredient per 100 kg seed | % infected heads | % Control |
|---|---|---|---|
| — | — | 13 | 0 |
| Racemic compound of formula Ia | 10 | 0 | 100 |
| Racemic compound C | 10 | 11.6 | 11 |

The results show that, at an application rate of 10 g active ingredient per 100 kg seed, the racemic compound of formula Ia according to the present invention exerts a substantially better fungicidal action against *Ustilago nuda* on barley than racemic compound C from the prior art. In view of the structural similarity between the compounds, the enhanced action of the compounds according to the present invention were not to be expected.

What is claimed is:

1. A method of controlling phytopathogenic diseases on seeds of useful plants, which comprises applying to the seeds a fungicidally effective amount of a mixture of compounds of the formula Ic

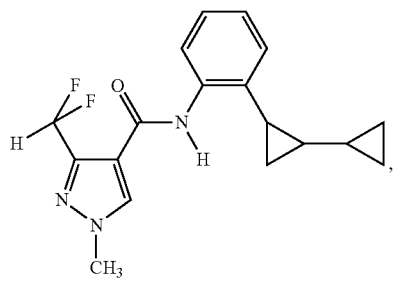

(Ic)

wherein the content of racemic compound of formula Ia (trans)

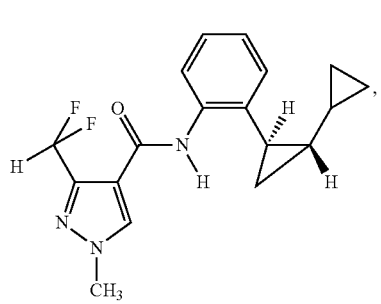

(Ia)

is from 65 to 99% by weight of the mixture, is applied to the seeds.

2. A method according to claim 1, comprising applying to the seeds a fungicidally effective amount of a plant propagation material protecting composition comprising the mixture, together with a suitable carrier.

3. A method according to claim 2, wherein said applying step comprises spraying or wetting the seeds with a liquid composition comprising the mixture, together with a suitable carrier.

4. A method according to claim 2, wherein said applying step comprises mixing the seeds with a solid composition comprising the mixture, together with a suitable carrier.

5. A method according to claim 2, wherein the plant propagation material protecting composition further comprises a water-soluble or water-dispersible film-forming polymer.

6. A seed treated with a plant propagation material protecting composition comprising a fungicidally effective amount of a mixture of compounds of the formula Ic

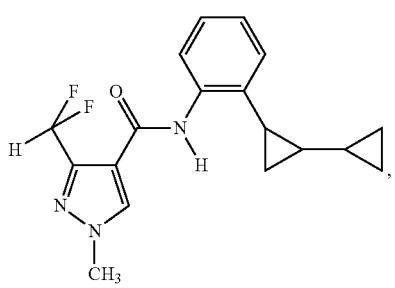

(Ic)

wherein the content of compounds of formula Ia (trans)

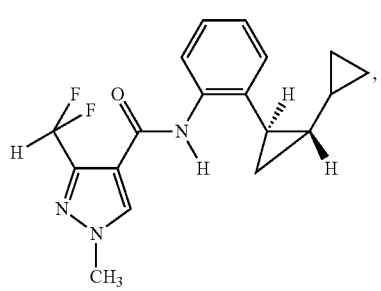

(Ia)

is from 65 to 99% by weight of the mixture, together with a suitable carrier.

7. The seeds according to claim 6, wherein said composition additionally comprises a coloring agent.

* * * * *